(12) United States Patent
Frutos et al.

(10) Patent No.: US 7,858,804 B2
(45) Date of Patent: Dec. 28, 2010

(54) PROCESS FOR MAKING CYTOKINE INHIBITING COMPOUNDS CONTAINING 4- AND 5-IMIDAZOLYL RINGS AND THE INTERMEDIATES THEREOF

(75) Inventors: Rogelio Perez Frutos, Sandy Hook, CT (US); Dhileepkumar Krishnamurthy, Brookfield, CT (US); Nitinchandra D. Patel, Danbury, CT (US); Sonia Rodriguez, New Milford, CT (US); Chris Hugh Senanayake, Brookfield, CT (US)

(73) Assignee: Boehringer Ingelheim International GmbH, Ingelheim Am Rhein (DE)

( * ) Notice: Subject to any disclaimer, the term of this patent is extended or adjusted under 35 U.S.C. 154(b) by 59 days.

(21) Appl. No.: 12/295,636

(22) PCT Filed: Apr. 16, 2007

(86) PCT No.: PCT/US2007/066684

§ 371 (c)(1),
(2), (4) Date: Oct. 1, 2008

(87) PCT Pub. No.: WO2007/121390

PCT Pub. Date: Oct. 25, 2007

(65) Prior Publication Data

US 2009/0137815 A1 May 28, 2009

Related U.S. Application Data

(60) Provisional application No. 60/745,010, filed on Apr. 18, 2006.

(51) Int. Cl.
C07D 403/04 (2006.01)
(52) U.S. Cl. .................................. 548/255; 548/300.1
(58) Field of Classification Search ................. 548/255, 548/300.1
See application file for complete search history.

(56) References Cited

FOREIGN PATENT DOCUMENTS

WO  2005/090333 A1  9/2005
WO  WO 2005/090333  *  9/2005

OTHER PUBLICATIONS

International Search Report for PCT/US07/066684 mailed Aug. 17, 2007.
R.P. Frutos, et al., "Expedient synthesis of substituted imidazoles from nitriles". Science Direct, Tetrahedron Letters, 46, 2005, pp. 8369-8372.
C.D. Smith, et al., "Synthesis of linked heterocycles via use of bis-acetylenic compounds". Science Direct, Tetrahedron Letters, 47, 2006, pp. 3209-3212.

* cited by examiner

*Primary Examiner*—Susannah Chung
(74) *Attorney, Agent, or Firm*—Michael P. Morris; Edward S. Lazer; Anthony P. Bottino

(57) ABSTRACT

Disclosed are processes for making compounds containing 4- and 5-imidazolyl rings, also disclosed are the intermediates useful in the processes disclosed herein.

1 Claim, No Drawings

PROCESS FOR MAKING CYTOKINE INHIBITING COMPOUNDS CONTAINING 4- AND 5-IMIDAZOLYL RINGS AND THE INTERMEDIATES THEREOF

APPLICATION DATA

This application is a 371 National Stage filing of PCT/US2007/066684 filed on Apr. 16, 2007. This application also claims benefit to U.S. provisional application Ser. No. 60/745,010 filed Apr. 18, 2006.

BACKGROUND OF THE INVENTION

1. Technical Field

This invention relates a process of making compounds useful as anti-inflammatory agents and intermediates thereof.

2. Background Information

WO 05/090333 discloses compounds of formula (I) and processes for preparing these compounds:

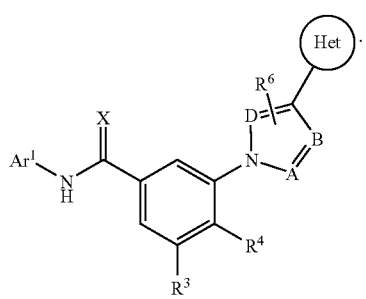

These compounds are useful for inhibition of the production of cytokines involved in inflammatory processes and for treating diseases and pathological conditions involving inflammation.

Particular product compounds containing imidazolyl rings were synthesized previously by a synthetic route shown below.

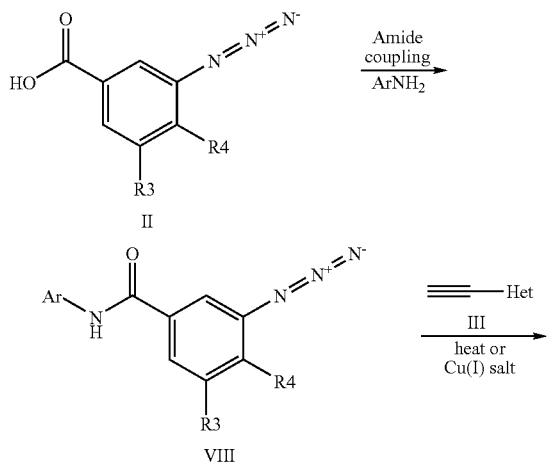

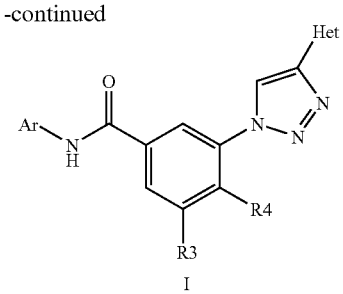

The amide coupling step is carried out with azide intermediate II to provide intermediate VIII. This is followed by reaction with the heteroaryl acetylene intermediate III in a suitable solvent such as EtOH, optionally in the presence of a copper salt such as $CuSO_4$ with an appropriate reductant such as sodium ascorbate, and optionally while heating to provide the desired compound of formula (I).

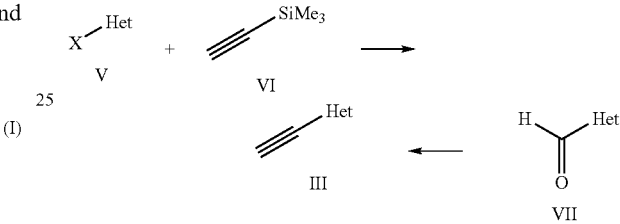

The heteroaryl acetylene intermediate III may be prepared by reaction of intermediate V, where X is I, Br, Cl or $-OSO_2CF_3$, with trimethylsilylacetylene VI, in the presence of a suitable catalyst such as $(PPh_3)PdCl_2$, a copper salt such as CuI and a suitable base such as $Et_3N$, followed by reaction with tetrabutylammonium bromide to remove the trimethylsilyl group. Alternatively, one may react a heteroaryl aldehyde VII with dimethyl 2-oxo-1-diazopropylphosphinate in the presence of a suitable base such as $K_2CO_3$ to provide intermediate III.

BRIEF SUMMARY OF THE INVENTION

It is an object of the invention to provide an improved process of making compounds of formula (Ia) containing 4- and 5-imidazolyl rings.

It is a further object of the invention to provide novel intermediates.

DETAILED DESCRIPTION OF THE INVENTION

In the broadest generic embodiment, there is provided a process of making compounds of the formula (Ia):

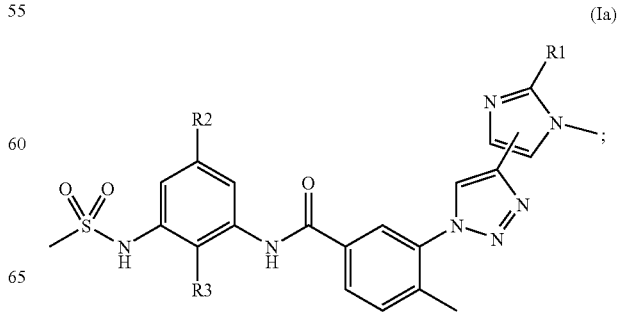

wherein:

the imidazole ring is substituted at the 4 or 5-position;

R1 is chosen from cyclopropyl, phenyl and 4-(CF$_3$)-phenyl;

R2 is chosen from tert-butyl, 1-methyl-cyclopropyl, hydrogen, 1-methoxycarbonyl-1-methyl-ethyl and 2-hydroxy-1,1-dimethyl-ethyl;

R3 is chosen from methoxy or hydrogen;

said process comprising:

i) combining haloimidazole 5 or its hydrochloride salt, a palladium catalyst such as PdCl$_2$(PPh$_3$)$_2$, CuI, an amine base such as Et$_3$N and trimethylsilylacetylene at a temperature of about 50° C., preferably for about 10 h in the presence of PPh$_3$ to produce alkyne 6;

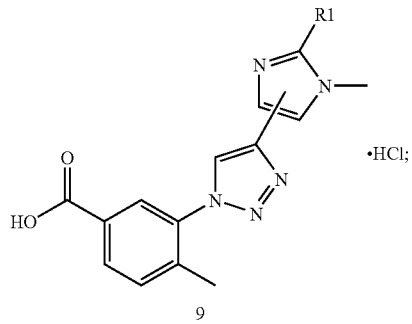

ii) combining NaN$_3$, 3-iodo-4-methyl benzoic acid (8):

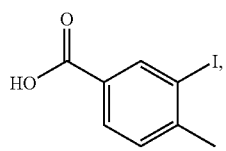

L-proline, a base such as Na$_2$CO$_3$, a Cu(I) source such as CuI or CuSO$_4$ in the presence of a reducing agent such as sodium ascorbate and DMSO and subsequently adding alkyne 6, and adding a suitable solvent and water to produce triazole 9;

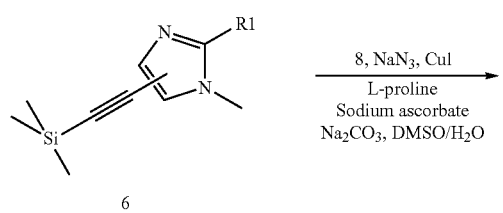

iii) treating triazole 9 with a suitable chlorinating agent such as oxalyl chloride or thionyl chloride in a suitable solvent such as acetonitrile or NMP containing DMF, and a suitable amine base such as pyridine; and subsequently adding amine

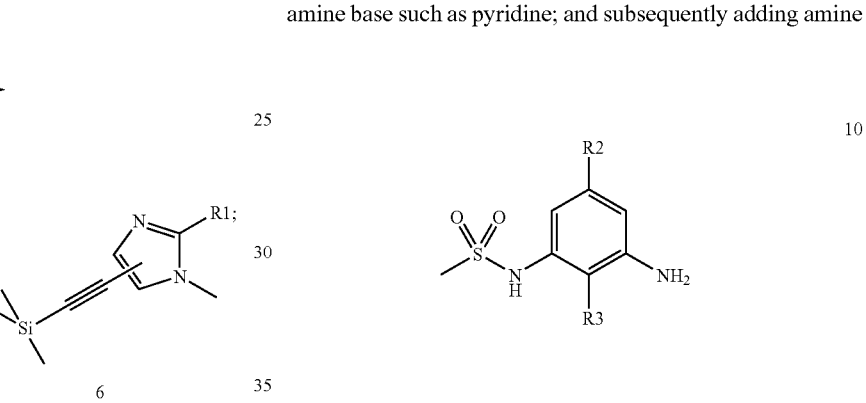

or its hydrochloride salt, in a suitable base such as DMAP and pyridine, to produce the product compound Ia:

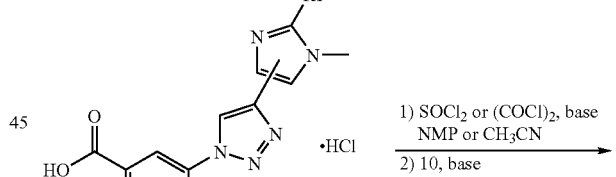

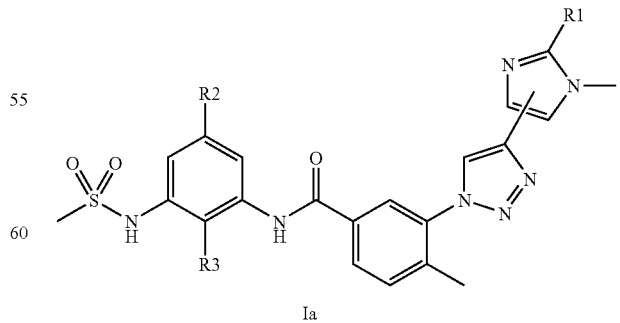

Haloimidazole 5, can be prepared according to the following general scheme:

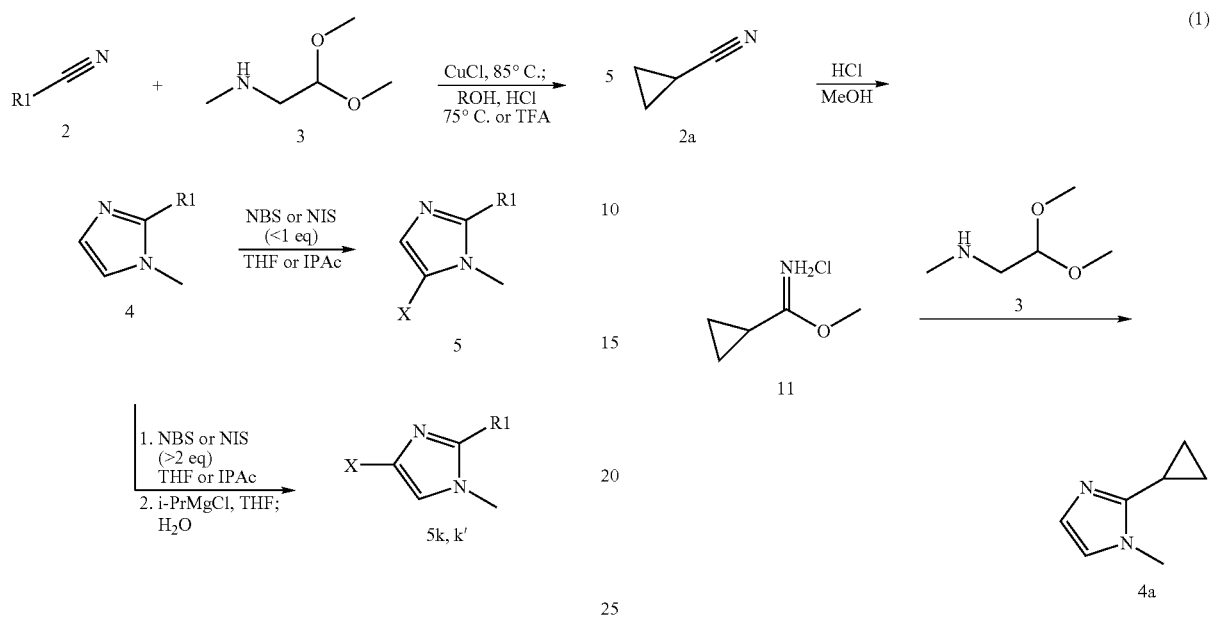

The imidazoles 4 were synthesized according to a modification of the published procedure (Frutos, R. P.; Gallou, I.; Reeves, D.; Xu, Y.; Krishnamurthy, D.; Senanayake, C. H. *Tetrahedron Lett.* 2005, 46, 8369). The above published procedure was modified by the introduction of thioamides, such as thioacetamide, as scavenging reagents to facilitate the removal of copper salts. Accordingly, a mixture of nitrile 2 and aminoacetal 3 is treated with a copper salt such as copper (I) chloride, and upon reaction completion, the copper salts are removed by filtration after addition of a thioamide such as thioacetamide, preferably prior to the cyclization of the intermediate amidine with HCl or TFA in an alcoholic solvent such as methanol or ethanol. Treatment of 4 with <1 eq of NBS or NIS under standard conditions provides the 5-haloimidazole 5. Treatment of 4 with >2 eq of NBS or NIS under standard conditions, followed by dehalogenation of the 4,5-dihaloimidazole intermediate with an alkylmagnesium halide salt such as i-PrMgCl provides 4-haloimidazole intermediates 5k and 5k'. Coupling of the desired haloimidazole to trimethylsilylacetylene using a modification of the known Sonogashira coupling (Sonogashira, K. *J. Organomet. Chem.* 2002, 653, 46) method provides intermediates such as 6, as shown above in step i). An alternative procedure (eq. 1) for the synthesis of imidazoles from imidates and α-amine-acetals is also known (Lawson, A. *J. Chem. Soc.* 1957, 4225) but its application for the synthesis of 4 has not been reported. The Cu-catalyzed synthesis of organic azides from aryl iodides has also been reported (Zhu, W.; Ma, D. *Chem. Commun.* 2004, 888), in our case the resulting azide intermediate is not isolated but treated with 8 directly to give 9, as shown above in step ii). The general synthesis of triazoles from alkanes and organic azides has been reported (Feldman, A. K.; Colasson, B.; Fokin, V. V. *Org. Lett.* 2004, 6, 3897), but not for a compound such as 9. The final coupling to give particular formula (I) compounds can be accomplished through the acyl chloride intermediate with different reagents ($SOCl_2$ in NMP, $(COCl)_2$ in acetonitrile), or using standard peptide coupling conditions (EDCI, mixed anhydrides, etc.).

EXPERIMENTAL

General Procedure for the Synthesis of Haloimidazoles (5):

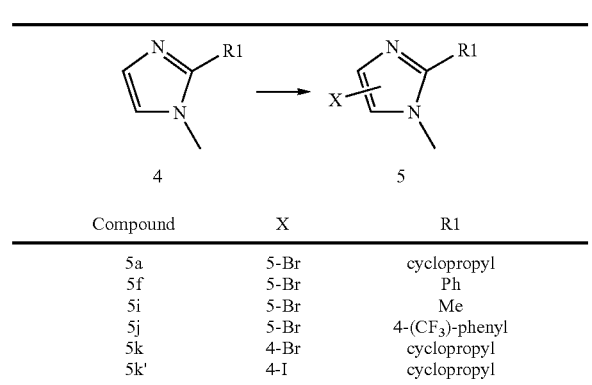

| Compound | X | R1 |
|---|---|---|
| 5a | 5-Br | cyclopropyl |
| 5f | 5-Br | Ph |
| 5i | 5-Br | Me |
| 5j | 5-Br | 4-($CF_3$)-phenyl |
| 5k | 4-Br | cyclopropyl |
| 5k' | 4-I | cyclopropyl |

A solution of imidazole 4 in isopropyl acetate was treated with $K_2CO_3$ (0.2 eq). After stirring for 5 min, NBS (0.95 eq) was added in portions. The reaction mixture was analyzed by HPLC after 2.5 h, and additional NBS was added if needed. The reaction mixture was quenched with water. The organic layer was washed with 5% $K_2CO_3$ and concentrated. The residue was dissolved in i-PrOH and treated with 5-6 M HCl in i-PrOH at room temperature overnight. The resulting solid was filtered, washed with i-PrOH and dried to afford 5.

The following examples were prepared by this method:

5-Bromo-2-cyclopropyl-1-methyl-1H-imidazole hydrochloride, 5a. 86% yield. Off-white solid. $^1$H-NMR (400 MHz, methanol-$d_4$) δ 7.60 (s, 1H), 3.87 (s, 3H), 2.29 (dt, J=8.0, 4.8

Hz, 1H), 1.6-1.28 (m, 2H), 1.18-1.11 (m, 2H); $^{13}$C-NMR (100 MHz, methanol-$d_4$) δ 151.1, 119.6, 109.0, 33.8, 7.7, 7.3.

5-Bromo-1-methyl-2-phenyl-1H-imidazole hydrochloride, 5f. 70% yield. Beige solid. $^1$H-NMR (400 MHz, methanol-$d_4$) δ 7.91 (s, 1H), 7.79-7.66 (m, 5H), 3.86 (s, 3H); $^{13}$C-NMR (100 MHz, methanol-$d_4$) δ 147.8, 134.0, 130.8, 130.7, 124.1, 121.4, 111.0, 35.9.

5-Bromo-1,2-dimethyl-1H-imidazole, 5i. 85% yield. Beige solid. $^1$H-NMR (400 MHz, CDCl$_3$) δ 6.89 (s, 1H), 3.51 (s, 3H), 2.41 (s, 3H).

5-Bromo-1-methyl-2-(4-trifluoromethyl-phenyl)-1H-imidazole, 5j. 77% yield. Yellow solid. $^1$H-NMR (400 MHz, CDCl$_3$) δ 7.74 (s, 4H), 7.17 (s, 1H), 3.72 (s, 3H); $^{13}$C-NMR (100 MHz,) δ 147.2, 134.0, 129.5, 128.8, 125.7, 125.7, 106.2, 33.5, 21.8.

4-Bromo-2-cyclopropyl-1-methyl-1H-imidazole hydrochloride, 5k. To a solution of 2-cyclopropyl-1-methyl-1H-imidazole (4a) (5.0 g, 40.9 mmol) in THF (75 mL) was added NBS (21.0 g, 122.7 mmol) in portions over a 1 h period. The solution was stirred at room temperature overnight, quenched with an aqueous solution containing 10% $K_2CO_3$ and 5% $Na_2S_2O_3$, and diluted with EtOAc. The aqueous layer was extracted with EtOAc, the combined organic layers were dried (MgSO$_4$), and concentrated affording crude 4,5-dibromo-2-cyclopropyl-1-methyl-1H-imidazole (18.8 g) which was purified by suspending it at room temperature in i-PrOH (20 mL) for 10 min. A solution of the resulting solid (7.0 g) in THF (90 mL) was cooled to –20° C. and treated with 2 M i-PrMgCl in THF (11.8 mL, 23.6 mmol) over a 1 h period. After stirring for 1 h, additional 2 M i-PrMgCl in THF (11.0 mL, 22.0 mmol) was added over 10 min, and the solution stirred for 10 more min. The reaction mixture was quenched with water, decanted and concentrated. The oil residue was diluted with EtOAc (60 mL), and the organic layer was washed with water twice, dried and concentrated. The oil was dissolved in i-PrOH (5 mL) and treated with 5-6 M HCl in i-PrOH (5 mL) over a 30 min period. After stirring overnight, the resulting solid was filtered, washed with i-PrOH and dried to afford 5k (5.23 g, 88% yield) as an off-white solid. $^1$H-NMR (400 MHz, methanol-$d_4$) δ 7.58 (s, 1H), 3.90 (s, 3H), 2.25 (dt, J=8.4, 5.2 Hz, 1H), 1.36-1.27 (m, 2H), 1.18-1.10 (m, 2H); $^{13}$C-NMR (100 MHz, methanol-$d_4$) δ 151.8, 124.7, 102.9, 35.3, 8.1, 6.4.

4-Iodo-2-cyclopropyl-1-methyl-1H-imidazole, 5k'. To a solution of 2-cyclopropyl-1-methyl-1H-imidazole (4a) (5.5 g, 45.0 mmol) in isopropyl acetate (110 mL) was added $K_2CO_3$ (1.25 g, 9.0 mmol) followed by NIS (40.3 g, 179.1 mmol) in portions over 2 h. The solution was stirred at 75° C. for 3 h, allowed to cool to room temperature and quenched with a 10% aqueous solution of $K_2CO_3$. The organic layer was washed with 10% $K_2CO_3$. The combined organic layers were concentrated affording crude 4,5-diiodo-2-cyclopropyl-1-methyl-1H-imidazole (10.5 g) as a dark solid. A solution of the resulting solid in THF (100 mL) was cooled to –20° C. and treated with 2 M i-PrMgCl in THF (17.5 mL, 35.0 mmol) dropwise. The reaction mixture was quenched with water and filtered. The organic layer was washed with brine and water, and concentrated afford 5k' (8.64 g, 77% yield) as a dark orange oil. $^1$H-NMR (400 MHz, CDCl$_3$) δ 6.85 (s, 1H), 3.66 (s, 3H), 1.74 (dt, J=8.4, 5.2 Hz, 1H), 1.03-0.91 (m, 4H); $^{13}$C-NMR (100 MHz, CDCl$_3$) δ 151.9, 125.8, 79.1, 32.5, 6.9, 6.8.

General procedure for the synthesis of 3H-imidazolyl-4-yl triazoles (9)

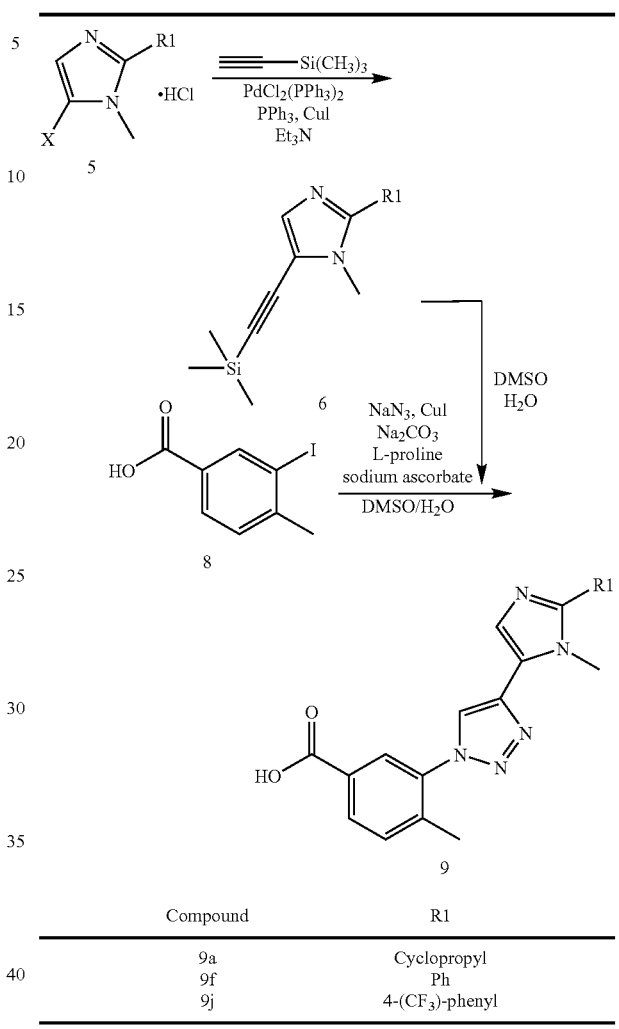

| Compound | R1 |
|---|---|
| 9a | Cyclopropyl |
| 9f | Ph |
| 9j | 4-(CF$_3$)-phenyl |

A mixture of haloimidazole 5, PPh$_3$ (3 mol %), PdCl$_2$(PPh$_3$)$_2$ (1.5 mol %), CuI (3 mol %), Et$_3$N (10 eq) and trimethylsilylacetylene (1.2 eq) was stirred at 50° C. for 10 h. After distilling most of the Et$_3$N, MTBE (t-butyl methyl ether) was added and distillation was continued. The mixture was suspended in MTBE and filtered through a pad of silica gel and charcoal to remove solids. 2 M aqueous HCl was added until pH 3. After adding n-Bu$_3$P (0.2 eq), the mixture was stirred for 1 h. The organic layer was extracted twice with 2 M aqueous HCl. The combined aqueous layers were basified to pH 10-11 with NH$_4$OH and extracted with MTBE. The organic layer was concentrated under vacuum to afford alkyne 6 as oily brown solid. In a different flask, an aqueous solution of NaN$_3$ (1.2 eq) was added to a mixture of 3-iodo-4-methyl benzoic acid (1.05 eq), L-proline (0.21 eq), Na$_2$CO$_3$ (1.26 eq), CuI (5 mol %), sodium ascorbate (5 mol %) and DMSO. After stirring at 85° C. for 10 h, the reaction mixture was allowed to cool to 20-25° C. Alkyne 6, DMSO and water were added, and the mixture stirred at 75° C. for 1.5 h. After filtering the mixture, the filter was rinsed with NH$_4$OH. The filtrate was poured onto a stirring cold solution of 2 M aqueous HCl, and the pH was adjusted to 4. The resulting precipitate was filtered, washed with water and allowed to air dry before being suspended in i-PrOH. n-Bu$_3$P (0.2 eq) was added and the mixture stirred at 80° C. for 1 h. After cooling to room temperature, the solid was filtered, washed with i-PrOH and dried to yield triazole 9 as solid.

The following examples were prepared by this method:

3-[4-(2-Cyclopropyl-3-methyl-3H-imidazol-4-yl)-[1,2,3] triazol-1-yl]-4-methyl-benzoic acid; hydrochloride, 9a. 45% yield. White solid. $^1$H-NMR (400 MHz, DMSO-d$_6$) δ 9.15 (s, 1H), 8.07 (dd, J=8.0, 1.6 Hz, 1H), 8.02 (d, J=1.6 Hz, 1H), 7.89 (s, 1H), 7.67 (d, J=8.0 Hz, 1H), 4.04 (s, 3H), 2.38 (dt, J=8.4, 5.2 Hz, 1H), 2.31 (s, 3H), 1.30-1.24 (m, 2H), 1.24-1.17 (m, 2H); $^{13}$C-NMR (100 MHz, DMSO-d$_6$) δ 166.1, 149.3, 138.4, 135.8, 135.1, 132.1, 130.7, 130.0, 126.7, 126.0, 124.7, 117.1, 33.2, 17.8, 7.5, 5.9.

4-Methyl-3-[4-(3-methyl-2-phenyl-3H-imidazol-4-yl)-[1,2,3]triazol-1-yl]-benzoic acid; hydrochloride, 9f. 30% yield. Light brown solid. $^1$H-NMR (400 MHz, methanol-d$_4$) δ 8.91 (s, 1H), 8.16 (d, J=4.0 Hz, 1H), 8.10 (d, J=5.2 Hz, 2H), 7.89-7.82 (m, 2H), 7.81-7.69 (m, 3H), 7.64 (d, J=8.0 Hz, 1H), 4.11 (s, 3H), 2.37 (s, 3H); $^{13}$C-NMR (100 MHz, methanol-d$_4$) δ 168.1, 147.8, 140.5, 137.4, 136.4, 133.8, 133.2, 132.5, 131.5, 130.9, 130.8, 128.34, 128.26, 127.6, 124.1, 119.4, 35.8, 18.3.

Synthesis of 1H-imidazol-4-yl triazole (9k)

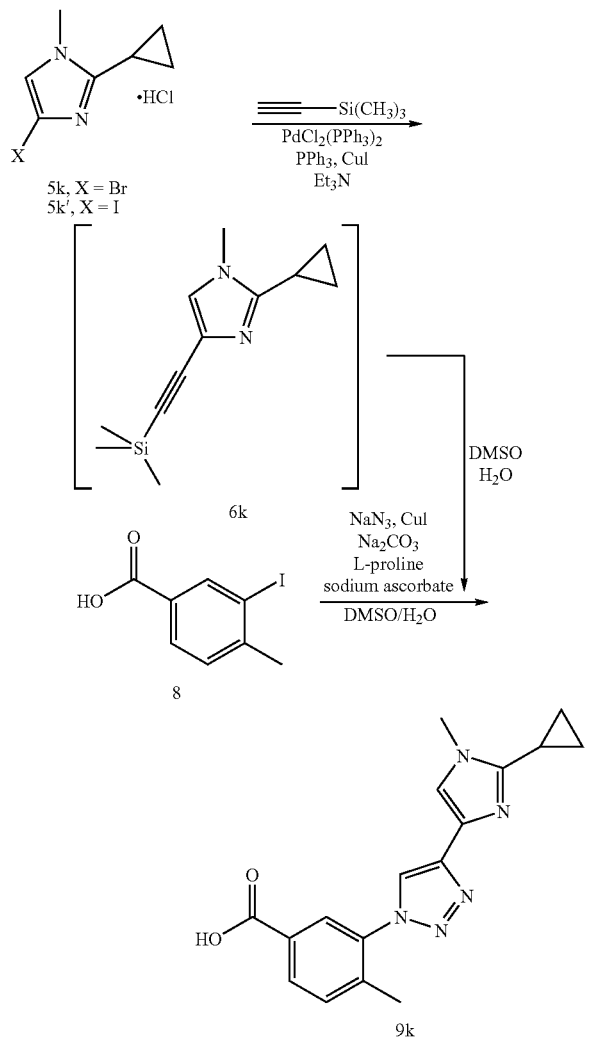

3-[4-(2-Cyclopropyl-1-methyl-1H-imidazol-4-yl)-[1,2,3] triazol-1-yl]-4-methyl-benzoic acid; hydrochloride, 9k. 15% yield. Light brown solid. $^1$H-NMR (400 MHz, methanol-d$_4$) δ 8.66 (s, 1H), 8.14 (dd, J=8.0, 1.6 Hz, 1H), 8.05 (d, J=1.2 Hz, 1H), 7.84 (s, 1H), 7.62 (d, J=8.0 Hz, 1H), 3.98 (s, 3H), 2.32 (s, 3H), 2.31-2.25 (m, 1H), 1.39-1.31 (m, 2H), 1.28-1.22 (m, 2H); $^{13}$C-NMR (100 MHz, methanol-d$_4$) δ 168.1, 150.8, 140.3, 137.4, 137.3, 133.1, 132.4, 131.5, 128.2, 125.3, 124.4, 121.2, 35.1, 18.2, 8.0, 6.5.

General Procedure for the Preparation of Amides (1):

A suspension of carboxylic acid 9 (300 mg) in anhydrous acetonitrile (5 mL) containing DMF (1 drop) was cooled to 10° C. Oxalyl chloride (1.5 eq) and pyridine (1.2 eq) were added slowly. The reaction mixture was allowed to stir at room temperature for 1 h. After distillation under vacuum, the residue was dissolved in acetonitrile (5 mL), and treated with the desired amine (1.0 eq), DMAP (3 mol %) and pyridine (0.4 eq). The reaction was stirred at room temperature for 16 h. The mixture was dissolved in warm EtOAc, washed with 25% K$_3$PO$_4$, dried (MgSO$_4$) and concentrated. Purification using combiflash (3-5% MeOH in CH$_2$Cl$_2$) afforded the desired amide.

The following examples were prepared by this method:

N-(5-tert-Butyl-3-methanesulfonylamino-2-methoxy-phenyl)-3-[4-(2-cyclopropyl-3-methyl-3H-imidazol-4-yl)-[1,2,3]triazol-1-yl]-4-methyl-benzamide, 1a. 85-90% yield. White solid. $^1$H-NMR (400 MHz, DMSO-d$_6$) δ 10.03 (s, 1H), 9.17 (s, 1H), 8.83 (s, 1H), 8.15 (s, 1H), 8.12 (dd, J=8.0, 1.6 Hz, 2H), 7.68 (d, J=8.0 Hz, 1H), 7.44 (d, J=2.0 Hz, 1H), 7.26 (d, J=2.4 Hz, 1H), 3.89 (s, 3H), 3.70 (s, 3H), 3.17 (d, J=5.2 Hz, 1H), 3.05 (s, 3H), 2.32 (s, 3H), 1.27 (s, 9H), 1.02-0.95 (m, 4H); $^{13}$C-NMR (100 MHz, DMSO-d$_6$) δ 164.1, 145.9, 144.9, 137.0, 136.0, 133.1, 131.8, 130.6, 130.2, 129.0, 125.3, 123.5, 120.9, 119.2, 60.5, 34.2, 31.1, 17.7, 6.8.

3-[4-(2-Cyclopropyl-3-methyl-3H-imidazol-4-yl)-[1,2,3] triazol-1-yl]-N-[3-methanesulfonylamino-2-methoxy-5-(1-methyl-cyclopropyl)-phenyl]-4-methyl-benzamide, 1b. 84% yield. Off-white solid. $^1$H-NMR (400 MHz, methanol-d$_4$) δ 8.56 (s, 1H), 8.13-8.03 (m, 2H), 7.65 (d, J=8.0 Hz, 1H), 7.48 (d, J=2.0 Hz, 1H), 7.27 (d, J=2.4 Hz, 1H), 7.16 (s, 1H), 3.94 (s, 3H), 3.78 (s, 3H), 3.03 (s, 3H), 2.36 (s, 3H), 2.03 (dt, J=8.4, 5.2 Hz, 1H), 1.39 (s, 3H), 1.08-0.99 (m, 2H), 0.97-0.91 (m, 2H), 0.87-0.80 (m, 2H), 0.76-0.70 (m, 2H); $^{13}$C-NMR (100 MHz, methanol-d$_4$) δ 167.0, 153.0, 144.8, 144.5, 139.6, 139.5, 137.8, 134.7, 133.2, 132.0, 131.8, 130.2, 127.0, 126.6, 125.1, 124.5, 121.9, 120.0, 61.6, 40.2, 32.2, 25.9, 20.6, 18.1, 16.2, 8.0, 7.1.

3-[4-(2-Cyclopropyl-3-methyl-3H-imidazol-4-yl)-[1,2,3] triazol-1-yl]-N-(3-methanesulfonylamino-phenyl)-4-methyl-benzamide, 1c. 18% yield. Beige solid. $^1$H-NMR (400 MHz, DMSO-d$_6$) δ 10.42 (s, 1H), 9.82 (s, 1H), 8.84 (s, 1H), 8.15 (d, J=1.6 Hz, 1H), 8.12 (dd, J=8.0, 2.0 Hz, 1H), 7.77-7.72 (m, 1H), 7.68 (d, J=8.0 Hz, 1H), 7.55 (bd, J=8.0 Hz, 1H), 7.31 (t, J=8.0 Hz, 1H), 7.12 (s, 1H), 6.95 (dd, J=8.0, 1.6 Hz, 1H), 3.88 (s, 3H), 3.01 (s, 3H), 2.31 (s, 3H), 2.06 (dt, J=8.0, 4.8 Hz, 1H), 0.98-0.90 (m, 2H), 0.90-0.82 (m, 2H); $^{13}$C-NMR (100 MHz, DMSO-d$_6$) 163.9, 150.8, 139.8, 138.7, 138.2, 137.0, 135.9, 133.5, 131.7, 129.4, 129.2, 126.2, 125.2, 123.5, 122.9, 115.9, 115.3, 111.7, 31.3, 17.7, 7.0, 6.8.

2-(3-{3-[4-(2-Cyclopropyl-3-methyl-3H-imidazol-4-yl)-[1,2,3]triazol-1-yl]-4-methyl-benzoylamino}-5-methanesulfonylamino-4-methoxy-phenyl)-2-methyl-propionic acid methyl ester, 1d. 16% yield. Beige solid. $^1$H-NMR (400 MHz, methanol-d$_4$) δ 8.83 (s, 1H), 8.16-8.06 (m, 2H), 7.76 (s, 1H), 7.69 (d, J=8.0 Hz, 1H), 7.61 (d, J=2.0 Hz, 1H), 7.38 (d, J=2.4 Hz, 1H), 4.14 (s, 3H), 3.82 (s, 3H), 3.67 (s, 3H), 3.05 (s, 3H), 2.38 (s, 3H), 2.38-2.28 (m, 1H), 1.56 (s, 6H), 1.39-1.31 (m, 2H), 1.22-1.16 (m, 2H); $^{13}$C-NMR (100 MHz, methanol-d$_4$) δ 178.3, 167.0, 151.2, 145.3, 142.4, 139.6, 137.6, 136.7, 134.8, 133.3, 132.3, 132.0, 130.4, 127.2, 126.8, 120.9, 119.1, 118.6, 61.7, 52.9, 47.7, 40.2, 34.1, 27.0, 18.2, 7.7, 6.9.

3-[4-(2-Cyclopropyl-3-methyl-3H-imidazol-4-yl)-[1,2,3]triazol-1-yl]-N-[5-(2-hydroxy-1,1-dimethyl-ethyl)-3-methanesulfonylamino-2-methoxy-phenyl]-4-methyl-benzamide, 1e. 21% yield. Beige solid. $^1$H-NMR (400 MHz, methanol-d$_4$) δ 8.58 (s, 1H), 8.18-8.03 (m, 2H), 7.67 (d, J=8.0 Hz, 1H), 7.59 (s, 1H), 7.45 (s, 1H), 7.20 (bs, 1H), 3.96 (s, 3H), 3.80 (s, 3H), 3.56 (s, 3H), 3.05 (s, 3H), 2.37 (s, 3H), 2.02 (s, 1H), 1.30 (s, 6H), 1.13-0.90 (m, 4H); $^{13}$C-NMR (100 MHz, methanol-d$_4$) δ 167.2, 145.2, 139.5, 137.8, 134.7, 133.2, 131.8, 131.5, 130.2, 126.8, 126.6, 125.2, 122.1, 120.2, 73.0, 61.6, 41.0, 40.1, 25.8, 18.1, 7.0.

N-(5-tert-Butyl-3-methanesulfonylamino-2-methoxy-phenyl)-4-methyl-3-[4-(3-methyl-2-phenyl-3H-imidazol-4-yl)-[1,2,3]triazol-1-yl]-benzamide, 1f. 59% yield. Tan solid. $^1$H-NMR (400 MHz, methanol-d$_4$) δ 8.67 (s, 1H), 8.10 (m, 2H), 7.71-7.64 (m, 3H), 7.62 (d, J=2 Hz, 1H), 7.58-7.50 (m, 3H), 7.48-7.41 (m, 2H), 3.93 (s, 3H), 3.79 (s, 3H), 3.04 (s, 3H), 2.86 (s, 3H), 1.32 (s, 9H); $^{13}$C-NMR (100 MHz, methanol-d$_4$) δ 167.1, 151.2, 148.7, 144.8, 139.5, 137.8, 134.8, 133.2, 131.8, 131.5, 131.2, 130.6, 130.2, 129.9, 128.6, 126.6, 126.2, 125.5, 121.0, 119.3, 61.6, 40.1, 35.6, 34.5, 31.7.

N-(3-Methanesulfonylamino-phenyl)-4-methyl-3-[4-(3-methyl-2-phenyl-3H-imidazol-4-yl)-[1,2,3]triazol-1-yl]-benzamide, 1g. 91% yield. Off-white solid. $^1$H-NMR (400 MHz, methanol-d$_4$) δ 8.67 (s, 1H), 8.14-8.06 (m, 2H), 7.71-7.63 (m, 3H), 7.58-7.41 (m, 5H), 7.28 (d, J=2.0 Hz, 1H), 3.92 (s, 3H), 3.78 (s, 3H), 3.03 (s, 3H), 2.38 (s, 3H), 1.39 (s, 3H), 0.87-0.82 (m, 2H), 0.76-0.71 (m, 2H); $^{13}$C-NMR (100 MHz, methanol-d$_4$) δ 167.0, 151.2, 144.8, 144.5, 139.5, 137.8, 134.7, 133.2, 132.0, 131.8, 131.2, 130.6, 130.2, 129.9, 128.6, 126.6, 126.2, 125.5, 121.9, 119.9, 61.6, 40.2, 34.5, 25.9, 20.6, 18.2, 16.3.

N-[3-Methanesulfonylamino-2-methoxy-5-(1-methyl-cyclopropyl)-phenyl]-4-methyl-3-[4-(3-methyl-2-phenyl-3H-imidazol-4-yl)-[1,2,3]triazol-1-yl]-benzamide, 1 h. 53% yield. Yellow solid. $^1$H-NMR (400 MHz, methanol-d$_4$) δ 8.62 (s, 1H), 8.06 (s, 1H), 8.08-8.02 (m, 1H), 7.77 (t, J=2 Hz, 1H), 7.66 (dd, J=7.8, 1.4, 2H), 7.61 (d, J=8.4 Hz, 1H), 7.57-7.49 (m, 3H), 7.44 (s, 1H), 7.48-7.40 (m, 1H), 7.29 (t, J=8 Hz, 1H), 7.01 (ddd, J=8.0, 2.0, 1.0 Hz, 1H), 3.91 (s, 3H), 2.98 (s, 3H), 2.35 (s, 3H); $^{13}$C-NMR (100 MHz, methanol-d$_4$) δ 166.8, 151.2, 140.8, 140.1, 139.4, 139.2, 137.6, 135.2, 133.1, 131.2, 130.7, 130.6, 130.3, 130.2, 129.9, 128.6, 126.5, 126.2, 125.4, 118.1, 117.4, 114.0, 39.3, 34.5, 18.1.

N-(5-tert-Butyl-3-methanesulfonylamino-2-methoxy-phenyl)-4-methyl-3-{4-[3-methyl-2-(4-trifluoromethyl-phenyl)-3H-imidazol-4-yl]-[1,2,3]triazol-1-yl}-benzamide, 1j. 50% yield. Yellow solid. $^1$H-NMR (400 MHz, methanol-d$_4$) δ 8.70 (s, 1H), 8.11 (bs, 2H), 7.91 (d, J=8.0 Hz, 1H), 7.86 (d, J=8.4 Hz, 1H), 7.67 (d, J=8.4 Hz, 1H), 7.62 (s, 1H), 7.51 (s, 1H), 7.43 (d, J=0.8 Hz, 1H), 3.98 (s, 3H), 3.79 (s, 3H), 3.04 (s, 3H), 2.38 (s, 3H), 1.31 (s, 9H); $^{13}$C-NMR (100 MHz, methanol-d$_4$) δ 167.1, 149.6, 148.7, 144.7, 139.5, 139.2, 137.8, 134.9, 134.8, 133.2, 131.7, 131.5, 130.8, 130.2, 129.1, 127.1, 126.82, 126.79, 126.6, 125.7, 121.0, 119.2, 61.6, 40.1, 35.6, 34.7, 31.7, 18.2.

N-(5-tert-Butyl-3-methanesulfonylamino-2-methoxy-phenyl)-3-[4-(2-cyclopropyl-1-methyl-1H-imidazol-4-yl)-[1,2,3]triazol-1-yl]-4-methyl-benzamide, 1k. 70% yield. Yellow solid. $^1$H-NMR (400 MHz, DMSO-d$_6$) δ 10.06 (s, 1H), 9.19 (s, 1H), 8.61 (s, 1H), 8.15 (s, 1H), 8.08 (d, J=8.0 Hz, 1H), 7.65 (d, J=8.0 Hz, 1H), 7.55 (bs, 1H), 7.44 (d, J=2.0 Hz, 1H), 7.26 (d, J=2.0 Hz, 1H), 3.75 (s, 3H), 3.70 (s, 3H), 3.01 (s, 3H), 2.33 (s, 3H), 1.99 (bs, 1H), 1.27 (s, 9H), 1.07-0.70 (m, 4H); $^{13}$C-NMR (100 MHz, DMSO-d$_6$) δ 164.2, 145.9, 144.8, 136.9, 133.0, 131.8, 130.6, 130.2, 128.8, 125.0, 121.0, 119.1, 60.6, 40.4, 34.2, 31.1, 17.9, 6.7.

3-[4-(2-Cyclopropyl-1-methyl-1H-imidazol-4-yl)-[1,2,3]triazol-1-yl]-N-[3-methanesulfonylamino-2-methoxy-5-(1-methyl-cyclopropyl)-phenyl]-4-methyl-benzamide, 11.79% yield. Yellow solid. $^1$H-NMR (400 MHz, methanol-d$_4$) δ 8.41 (bs, 1H), 8.14-8.00 (m, 2H), 7.66 (d, J=8.0 Hz, 1H), 7.47 (d, J=2.0 Hz, 1H), 7.28 (d, J=2.0 Hz, 1H), 3.82 (s, 3H), 3.78 (s, 3H), 3.03 (s, 3H), 2.35 (s, 3H), 2.03 (dt, J=15.2, 8.0 Hz, 1H), 1.39 (s, 3H), 1.12-0.94 (m, 4H), 0.85 (dd, J=6.2, 3.6 Hz, 2H), 0.74 (dd, J=5.6, 3.6 Hz, 2H); $^{13}$C-NMR (100 MHz, methanol-d$_4$) δ 167.1, 144.8, 144.5, 139.3, 134.8, 133.2, 132.0, 131.8, 130.2, 126.5, 121.9, 119.9, 61.6, 40.1, 31.7, 25.9, 20.6, 18.2, 16.3, 6.9.

3-[4-(2-Cyclopropyl-1-methyl-1H-imidazol-4-yl)-[1,2,3]triazol-1-yl]-N-(3-methanesulfonylamino-phenyl)-4-methyl-benzamide, 1m. 35% yield. Light orange solid. $^1$H-NMR (400 MHz, methanol-d$_4$) δ 8.35 (bs, 1H), 8.10-7.98 (m, 2H), 7.76 (s, 1H), 7.60 (d, J=8.0 Hz, 1H), 7.44 (dd, J=8.2, 1.0 Hz, 2H), 7.30 (t, J=8.0 Hz, 1H), 7.02 (dd, J=8.2, 1.4 Hz, 1H), 3.79 (s, 3H), 2.98 (s, 3H), 2.31 (s, 3H), 1.97 (bs, 1H), 1.10-0.88 (m, 4H); $^{13}$C-NMR (100 MHz, methanol-d$_4$) δ 166.9, 140.8, 140.1, 139.1, 137.8, 135.2, 133.1, 130.7, 130.2, 126.3, 122.8, 119.7, 118.1, 117.4, 114.0, 39.3, 33.2, 18.1, 7.7, 7.0.

The invention claimed is:

1. A process of making compounds of the formula (Ia):

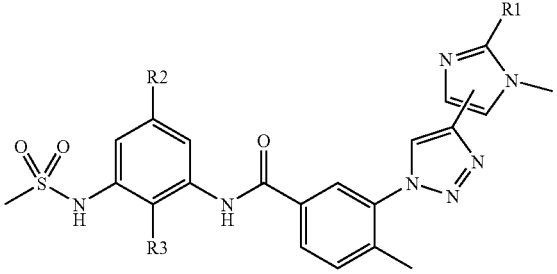

wherein:
the imidazole ring is substituted at the 4 or 5-position;
R1 is chosen from cyclopropyl, phenyl and 4-(CF$_3$)-phenyl;
R2 is chosen from tert-butyl, 1-methyl-cyclopropyl, hydrogen, 1-methoxycarbonyl-1-methyl-ethyl and 2-hydroxy-1,1-dimethyl-ethyl;
R3 is chosen from methoxy or hydrogen;
said process comprising:
i) combining haloimidazole 5 or its hydrochloride salt, a palladium catalyst, an amine base and trimethylsilylacetylene at a temperature of about 50° C., preferably for about 10 h in the presence of PPh$_3$ to produce alkyne 6;

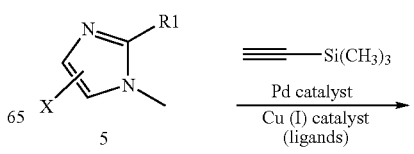

-continued

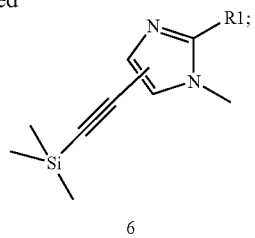

ii) combining NaN₃, 3-iodo-4-methyl benzoic acid (8):

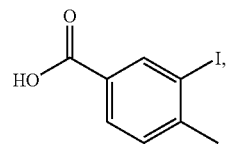

L-proline, a base such as Na₂CO₃, a Cu(I) source such as CuI or CuSO₄ in the presence of a reducing agent such as sodium ascorbate and DMSO and subsequently adding alkyne 6, and adding a suitable solvent and water to produce triazole 9;

iii) treating triazole 9 with a chlorinating agent selected from oxalyl chloride and thionyl chloride and a suitable amine base to produce the acid chloride; subsequently adding amine

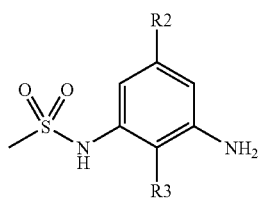

or its hydrochloride salt, and a suitable amine base, to produce the product compound Ia:

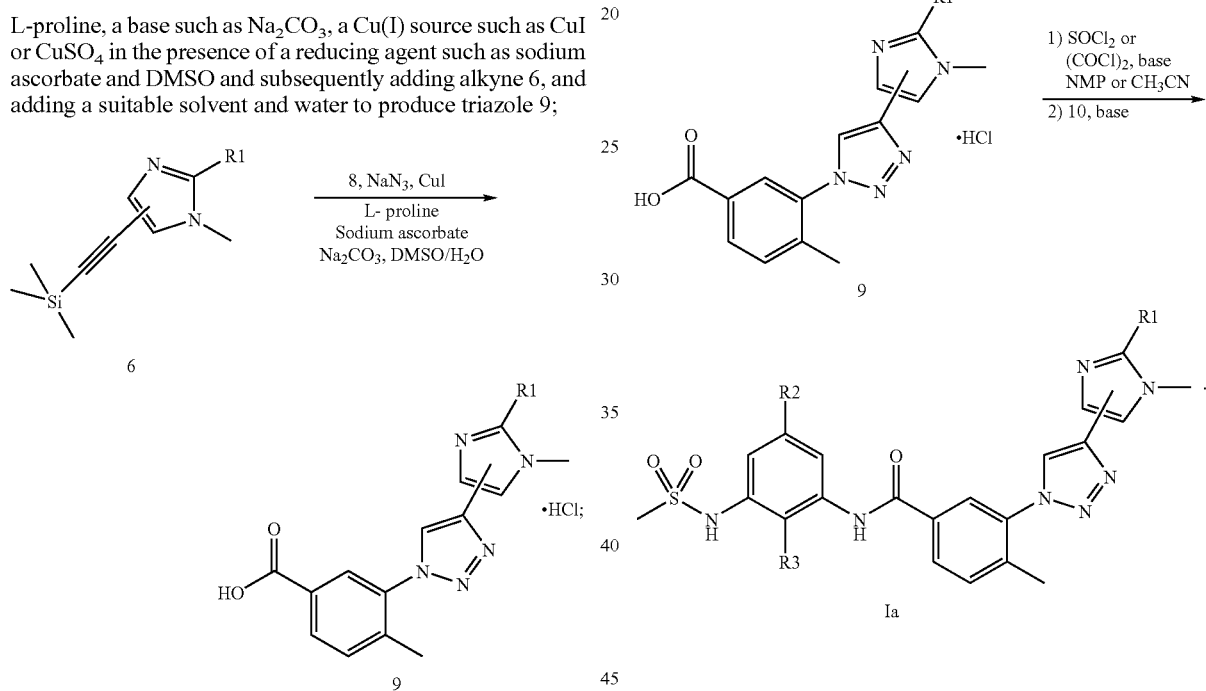

* * * * *